(12) United States Patent
Garner et al.

(10) Patent No.: US 8,635,731 B2
(45) Date of Patent: Jan. 28, 2014

(54) TEETHBRUSH

(76) Inventors: Robert Garner, Miami, FL (US); Heather Brundage, Cambridge, MA (US); Nathaniel Sharpe, Allston, MA (US); Alexis Hornstein, Raleigh, NC (US); James Brewster, Miami, FL (US)

( * ) Notice: Subject to any disclaimer, the term of this patent is extended or adjusted under 35 U.S.C. 154(b) by 74 days.

(21) Appl. No.: 13/182,414

(22) Filed: Jul. 13, 2011

(65) Prior Publication Data

US 2013/0014331 A1    Jan. 17, 2013

(51) Int. Cl.
*A61C 17/22* (2006.01)

(52) U.S. Cl.
USPC .............................................. 15/22.1; 15/22.2

(58) Field of Classification Search
USPC .................... 15/22.1, 22.2, 167.1, 167.2
See application file for complete search history.

(56) References Cited

U.S. PATENT DOCUMENTS

| | | | |
|---|---|---|---|
| 887,181 A | 5/1908 | Barnes | |
| 1,417,407 A | 5/1922 | Novak | |
| 1,707,118 A | 3/1929 | Goldberg | |
| 1,818,146 A | 8/1931 | Maker | |
| D196,635 S | 10/1963 | Kinsella | |
| 3,163,874 A | 1/1965 | Bauer | |
| 3,380,446 A | 4/1968 | Martin | |
| D221,272 S | 7/1971 | Splaine | |
| 3,731,675 A | 5/1973 | Kelly | |
| 3,769,652 A | 11/1973 | Rainer | |
| 4,011,616 A | 3/1977 | Kennedy | |
| 4,048,690 A | 9/1977 | Wolfson | |
| 4,224,710 A | 9/1980 | Solow | |
| 4,237,574 A | 12/1980 | Kelly et al. | |
| 4,348,178 A | 9/1982 | Kurz | |
| 4,538,315 A | 9/1985 | Barth | |
| 4,795,347 A | 1/1989 | Maurer | |
| 5,175,901 A | 1/1993 | Rabinowitz | |
| 5,177,827 A * | 1/1993 | Ellison | 15/22.1 |
| 5,337,435 A | 8/1994 | Krasner | |
| 5,365,624 A | 11/1994 | Berns | |
| 5,443,386 A | 8/1995 | Viskup | |
| 5,500,970 A | 3/1996 | Maurer et al. | |
| 5,615,443 A | 4/1997 | Lai | |
| 6,152,733 A | 11/2000 | Hegemann et al. | |
| 6,223,376 B1 | 5/2001 | Lee | |
| 6,353,956 B1 | 3/2002 | Berge | |
| 6,893,259 B1 | 5/2005 | Reizenson | |
| 7,044,737 B2 | 5/2006 | Fu | |
| 7,059,853 B2 | 6/2006 | Hegemann | |
| 7,082,638 B2 * | 8/2006 | Koh | 15/22.1 |
| 7,118,377 B2 | 10/2006 | Inoue et al. | |
| 7,757,328 B2 | 7/2010 | Hegemann et al. | |
| 7,802,989 B2 | 9/2010 | Schemmer | |
| 7,832,043 B1 | 11/2010 | Feldman | |
| 7,935,065 B2 | 5/2011 | Martin et al. | |
| 2005/0039280 A1 | 2/2005 | Trimmer et al. | |
| 2007/0204413 A1 | 9/2007 | Kuznetsov et al. | |
| 2009/0208898 A1 | 8/2009 | Kaplan | |
| 2010/0062397 A1 | 3/2010 | Brewer | |

FOREIGN PATENT DOCUMENTS

| | | |
|---|---|---|
| JP | 2009066370 | 4/2009 |
| WO | 2010143313 | 12/2010 |

* cited by examiner

*Primary Examiner* — Shay Karls
(74) *Attorney, Agent, or Firm* — Allen, Dyer, Doppelt, Milbrath & Gilchrist, P.A.

(57) ABSTRACT

A full mouth toothbrush for simultaneously brushing the facial, lingual, occlusal and incisal surfaces of all the maxillary and mandibular teeth is provided. The full mouth toothbrush can include a handle, a power source, a motor assembly, and a drive assembly. The full mouth toothbrush can further include a mouthpiece configured to collectively contact multiple surfaces of multiple teeth simultaneously that brushes and, thus, cleans the teeth and gums.

25 Claims, 13 Drawing Sheets

TEETHBRUSH

BACKGROUND OF THE INVENTION

1. Field of the Invention

The present invention relates to a toothbrush and more particularly to a toothbrush that brushes all teeth simultaneously.

2. Description of the Related Art

The toothbrush is an oral hygiene instrument used to remove plaque, clean teeth and stimulate the gums. The standard manual toothbrush consists of a bristled head attached to a handle, where the bristled head is only capable of cleaning a small area at a time. The recommend way to manually brush teeth is to use the Bass method, whereby the toothbrush is held such that the bristles are angled at a forty five degree angle to the long axis of the tooth and moved back and forth in short, quick strokes. This motion requires a certain level of dexterity often absent in the very young, the elderly and people with physical or mental limitations. Additionally, it is up to the user to ensure that each tooth surface is adequately cleaned. Since this is hard to determine, it is recommended that a person should brush for at least two minutes to effectively clean all the surfaces of his or her teeth. Unfortunately, many people do not have a good way to time their brushing routine and do not realize how long they have actually been brushing, thus resulting in shorter brushing sessions that fail to adequately remove plaque from all surfaces.

An electric toothbrush uses electric power to either move individual bristles ultrasonically or to move a brush head rapidly. By providing some motion electrically, electric toothbrushes augment the normal brushing capabilities of a person. Some electric toothbrushes even include a timer feature and/or automatically turn off after a set amount of time, like two minutes, in order to guide the user to use the toothbrush for the full recommended time. Though these capabilities encourage proper brushing, standard electric toothbrushes still require a user to move the toothbrush from tooth to tooth and to manipulate the toothbrush onto the surface of each tooth as only a small area of the mouth can be cleaned at once. As with a manual toothbrush, a person with limited manual dexterity may find using an electric toothbrush difficult or impossible because of the manipulation required to properly reach every tooth surface.

Regardless of whether a person uses a manual or an electric toothbrush, a person who is rushed, too tired, or physically or mentally impaired may not spend the recommended time brushing his or her teeth. He or she may also not be willing or able to adequately manipulate the toothbrush. Both of these deficiencies could result in inadequate toothbrushing and could lead to dental caries and gum disease.

BRIEF SUMMARY OF THE INVENTION

Embodiments of the present invention address deficiencies of the art in respect to full mouth toothbrushes and provide a novel and non-obvious apparatus for effectively brushing all faces of all teeth simultaneously. In an embodiment of the invention, a handle partially enclosing a power source, a motor assembly, and a drive assembly can be provided. An embodiment of the full mouth toothbrush can further include a mouthpiece driven in a brush motion by the drive assembly. The mouthpiece can include at least one bristle strip.

Additional aspects of the invention will be set forth in part in the description which follows, and in part will be obvious from the description, or may be learned by practice of the invention. The aspects of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE SEVERAL VIEWS OF THE DRAWINGS

The accompanying drawings, which are incorporated in and constitute part of this specification, illustrate embodiments of the invention and together with the description, serve to explain the principles of the invention. The embodiments illustrated herein are presently preferred, it being understood, however, that the invention is not limited to the precise arrangements and instrumentalities shown, wherein:

FIG. 4 shows front (A), top (B), and isometric (C) views of a posterior section of a bristle strip;

DETAILED DESCRIPTION OF THE INVENTION

Embodiments of the invention provide for a full mouth toothbrush that brushes the surfaces of multiple teeth simultaneously. In particular, through the use of the full mouth toothbrush, no user intervention is required to clean multiple surfaces of multiple teeth simultaneously after the full mouth toothbrush is placed in the mouth of a user, thereby allowing a person with limited manual dexterity, limited time, limited energy or other limitations to receive an effective cleaning. In accordance with an embodiment of the invention, the full mouth toothbrush can include a handle including a power source, for example a battery, a motor assembly powered by the power source that is coupled to a drive assembly, which is driven by the motor assembly. The handle can be adapted to both receive and secure a mouthpiece in place.

The mouthpiece can include a semi-elliptical frame, such as a u-shaped frame, with an aperture defined thereby. The mouthpiece can further include one or more bristle strips being configured to collectively contact multiple surfaces of multiple teeth simultaneously. A portion of the mouthpiece, for instance at least one bristle strip, can be actuated back and forth when contacting the teeth by way of the drive assembly disposed partially within the handle and partially within the mouthpiece. More specifically, the drive assembly can include a gear coupling a motor assembly with the approximate end of a pin. The opposite end of the pin can contact a face of a plate. The plate can be coupled to an approximate end of a rod that can be attached to the mouthpiece, where the motor assembly rotates the gear causing the pin to move linearly in a back and forth motion oscillating the plate forwards and backwards in order to cause the rod to move forwards and backwards thereby driving a portion of the mouthpiece forwards and backwards, for instance a bristle strip.

Figure 1:
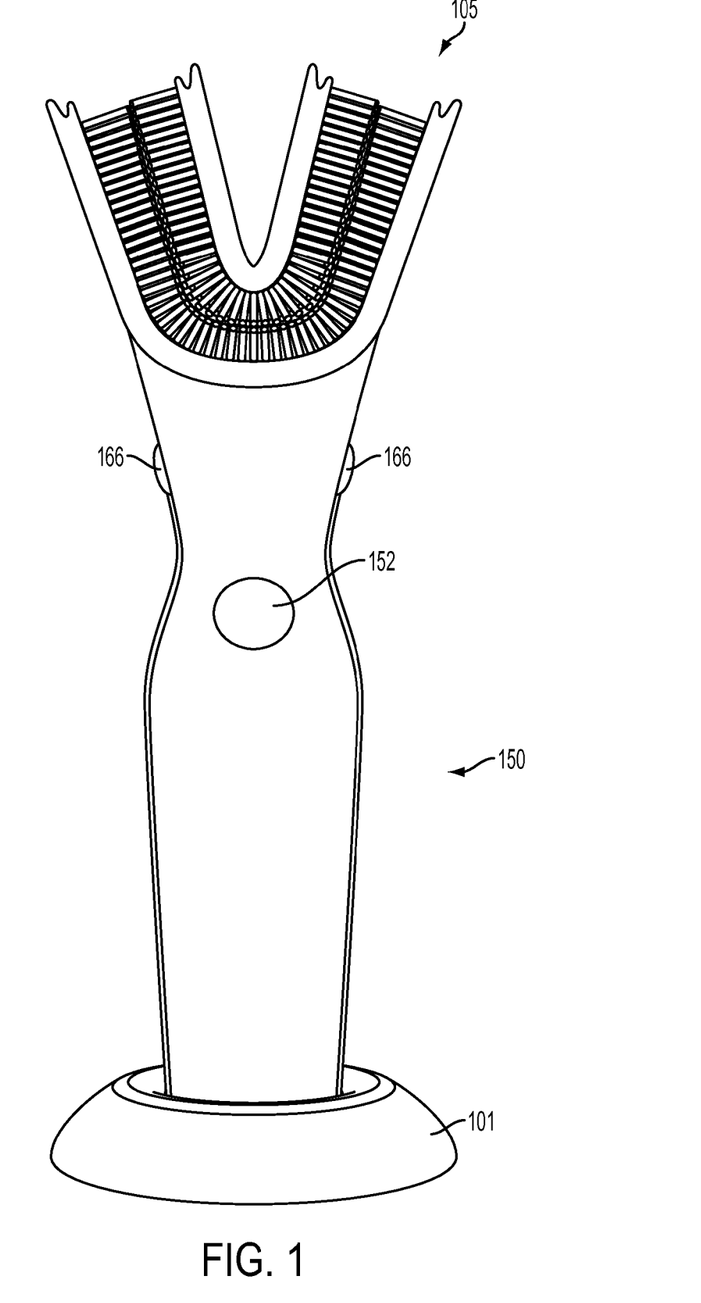
FIG. 1 shows an embodiment of an electric full mouth toothbrush.

In further illustration, FIG. 1 shows an embodiment of a full mouth electric toothbrush having a mouthpiece 105 that fits into a handle 150. In an embodiment, the mouthpiece 105 can include a semi-elliptical frame, such as a u-shaped frame, and can be detached from the handle 150 by eject buttons 166 after it is inserted into the handle 150. The handle 150 can have a power button 152 located on the handle 150. The power button 152 is not limited to a button, but can be a switch or such. The handle 150 is not limited to a specific build, make, or model, but must accept the mouthpiece 105. Of note, in another embodiment, there can be no handle 150. Of further note, in another embodiment, a handle 150 does not need to contain a power source or a motor assembly; the handle can be simple, for instance a rod, and can be coupled to a mouthpiece 105 for ease of placing and removing the mouthpiece 105 into the mouth of a user.

The handle 150 can optionally sit in a base 101. In one embodiment, the base 101 can have a power cord that plugs into an electrical outlet, which can serve as a conduit in recharging the power source located in the handle 150. In other words, the base 101 can wirelessly transmit energy through an induction charging coil to the handle 150, which can store (recharge) the energy in the power source. In another embodiment, the full mouth toothbrush may contain electrical contacts and have no induction coil and require charging via wires. The base 101 can be made of plastic. In another embodiment, the base 101 can serve as a holder and not as a charger.

Figure 2:
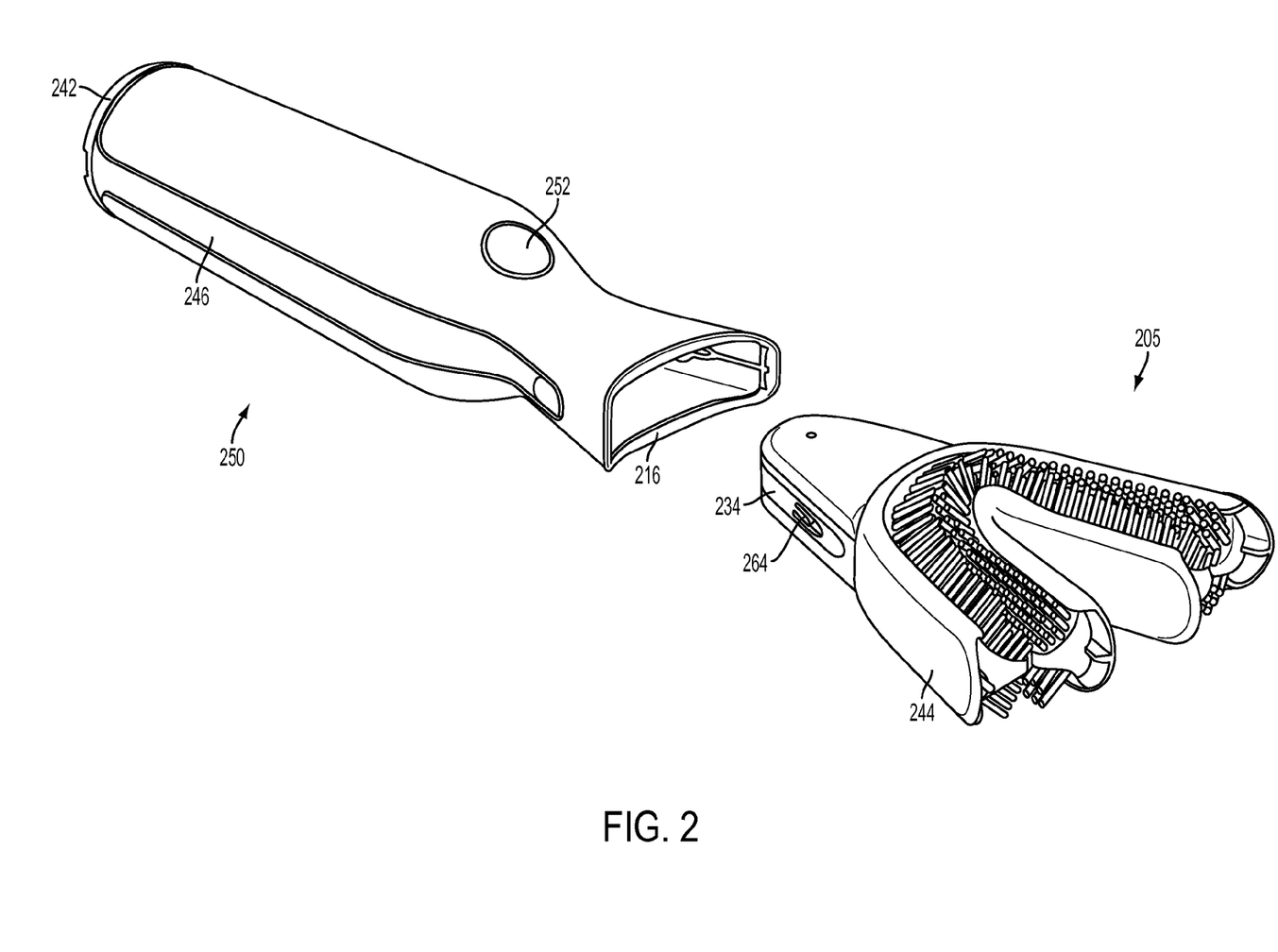
FIG. 2 illustrates an exploded view of a handle and a mouthpiece in an embodiment of a full mouth toothbrush.

In further illustration, FIG. 2 shows an exploded view of a handle 250 and a mouthpiece 205 in an embodiment of a full mouth toothbrush. The mouthpiece 205 can consist of a cover 234. In one instance, the cover 234 can be welded to the outer frame 244 of the mouthpiece 205. In another instance, there can be no cover 234 and at least one snap hook 264 can be integrated into the outer frame 244 during the manufacturing of the mouthpiece 205. At least one snap hook 264 on the mouthpiece 205 could enable the mouthpiece to be coupled to the handle 250. The semi-elliptical frame of the mouthpiece 205 at least partially fits inside the mouth of a user. More specifically, the mouthpiece 205 at least partially fits inside the mouth of a user while components of a drive assembly located inside the handle 250 and inside an outer frame of the mouthpiece 205 move bristle strips that can be part of the mouthpiece 205.

In an embodiment, the snap hooks 264 are located on the cover 234. During operation, the snap hooks 264 are pushed in (depressed) when the eject buttons on the handle 250 are pressed. In other words, the hard plastic of the handle 250 pushes in the snap hooks 264 when the eject button is pressed. In another embodiment, spring pins can replace snap hooks. The spring pins can be retractable and spring loaded, which can enable a user to snap the mouthpiece 205 into the handle 250 that has been configured to receive the mouthpiece 205. A user can then push eject buttons on the handle 250 to release the mouthpiece 205 allowing the mouthpiece 205 to be replaceable. In another embodiment, the mouthpiece 205 can be permanently attached to a handle 250 by any means, including but not limited to screws, pins, and glue. In other words, in some embodiments the mouthpiece 205 is replaceable (detachable), and in other embodiments, the mouthpiece 205 is permanently attached to the handle 250.

The mouthpiece 205 can slide into the handle 250. In addition to securing the mouthpiece 205 to the handle 250 via snap hooks 264, the handle 250 can have a gasket 216 to assist in creating a tight and secure fit between the mouthpiece 205 and the handle 250. In an embodiment, the gasket 216 can be made of plastic. More specifically, the gasket 216 can be made of a rubber-like material having a low enough durometer so as to be able to compress slightly upon the inserting of the mouthpiece 205. The handle 250 can have an overmolding 246 as well as a cap 242. In an embodiment, the cap 242 can be made of plastic and can be removed to allow proper disposal of the power source. The handle overmolding 246 can be made of plastic, including rubber, and can provide a more comfortable and secure grip to the user as well as provide a more aesthetic design.

Figure 3:
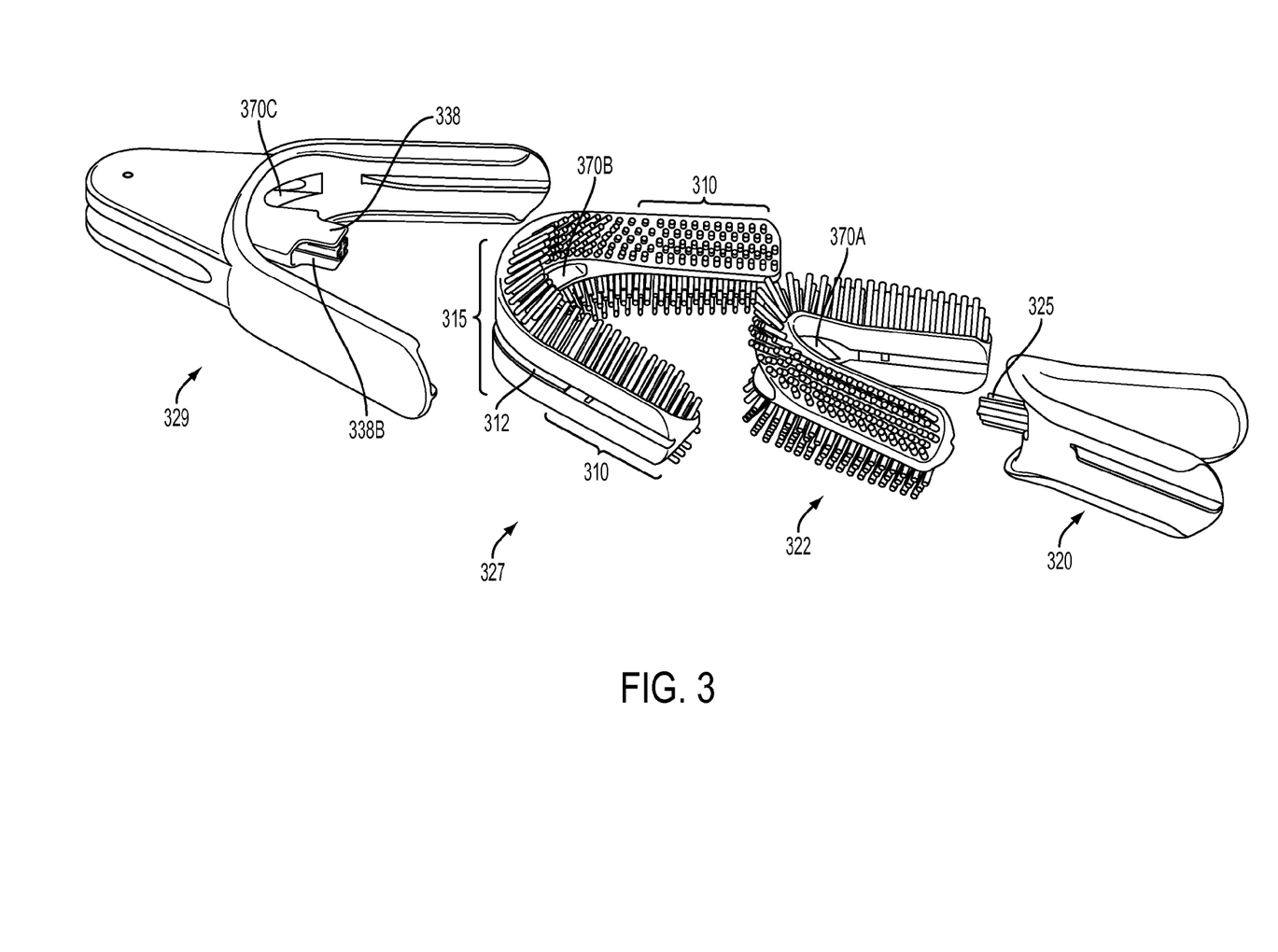
FIG. 3 is an exploded view of a mouthpiece.

In further illustration, an exploded view of the mouthpiece is shown in FIG. 3. In an embodiment, a semi-elliptical inner frame 320, such as a u-shaped frame, can have a connector 325 that fits through both an aperture 370A on an inner bristle strip 322 and an aperture 370B on an outer bristle strip 327 into a connector/protector 338 on a semi-elliptical outer frame 329, such as a u-shaped frame. The outer frame 329 can also have an aperture 370C that enables components of the drive assembly to pass through and reach the outer bristle strip 327. Also on the outer frame 329 can be additional apertures 338B, which enable components of the drive assembly to pass through and reach the inner bristle strip 322. Of note, the outer frame 329 can be configured to also receive components of the drive assembly.

The outer frame 329 and the inner frame 320 can be made of a hygienic plastic, such as polyoxymethylene (also known as acetal, polyacetal, and polyformaldehyde), but can be made out of a hygienic metal that does not rust, such as stainless steel. In addition, the outer frame 329 and inner frame 320 can also be made from ceramics, metals, natural materials or other plastics, including but not limited to polypropylene and acrylonitrile butadiene styrene (ABS). The method of joining the outer guard 329 and inner guard 320 is not limited to a specific method, such as press fit, but can be joined using any technique now known or later developed, including but not limited to plastic welding.

Coupled to the inner frame 320 can be an inner bristle strip 322 and coupled to the outer frame 329 can be an outer bristle strip 327. In an embodiment, the inner bristle strip 322 slides onto the inner frame 320; the inner bristle strip 322 cleans the lingual, occlusal, and incisal surfaces of the teeth. The outer bristle strip 327 can slide onto the outer frame 329; the outer bristle strip 327 can clean the facial, occlusal, and incisal surfaces of the teeth. Of note, the mouthpiece is tailored to fit the average mouth shape, but can be customized.

The inner bristle strip 322 and the outer bristle strip 327 are each similar in shape and design, but are not identical. They are slightly different to allow for the components of the mouthpiece to be nested as well as to allow the inner bristle strip 322 to clean the lingual, occlusal, and incisal surfaces of the teeth and the outer bristle strip 327 to clean the facial, occlusal, and incisal surfaces of the teeth. Of note, the combination of the inner and outer bristle strips 322, 327 is designed to clean multiple surfaces of each tooth.

The configuration of each bristle strip is not limited to a specific iteration. In one embodiment, the inner bristle strip 322 and the outer bristle strip 327 can each be composed of two posterior sections 310 located on the approximate end of each bristle strip and an anterior section 315 located in the approximate middle between the posterior sections. The anterior section 315 is largely responsible for cleaning the anterior teeth, and the posterior section 310 is largely responsible for cleaning the posterior teeth. Of note, in one embodiment, the posterior section 310 is approximately rigid and approximately straight. Of further note, in one embodiment, the anterior section 315 can be flexible and curved. The anterior section 315 and the posterior sections 310 are bonded together.

In an embodiment, the anterior section 315 can also have a cutout 312, which allows outer rods of the drive assembly to reach the posterior sections of the bristle strip. The anterior section 315 can also have at least one aperture that enables any inner rod of the drive assembly to reach the posterior sections of the bristle strip. In an embodiment, each bristle strip can be built as three separate pieces and joined into one; the anterior section 315 and the posterior sections 310 are bonded together by modeling the posterior section 310 with a post over which the anterior section 315 is molded. In another embodiment, each bristle strip could be composed of a continuous strip of a homogeneous material. The bristle strip can also be flexible throughout (as opposed to being composed of at least one posterior section). A bristle strip can also be solid and hinged throughout; it can also be like a bike chain.

Figure 4A:
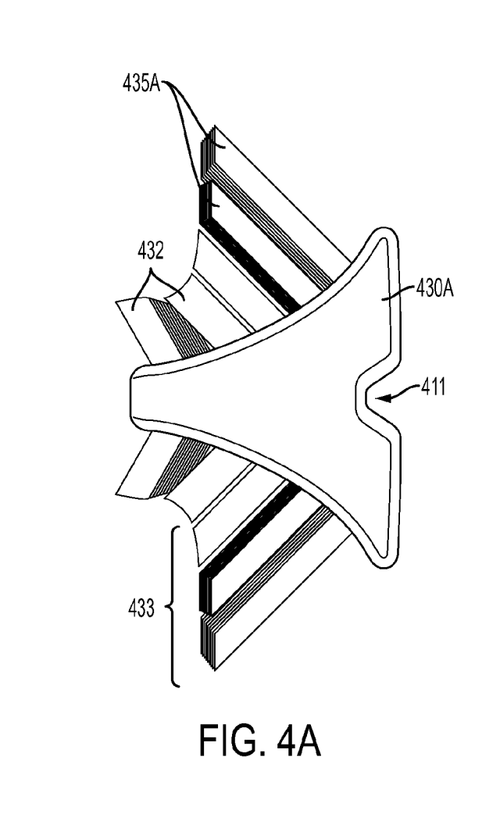
Figure 4B:
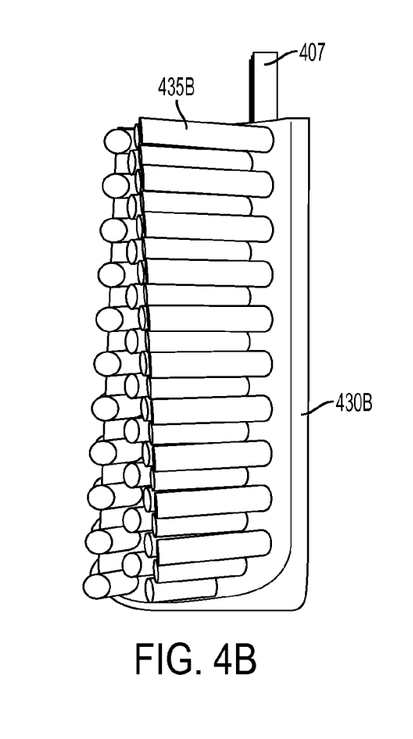
Figure 4C:
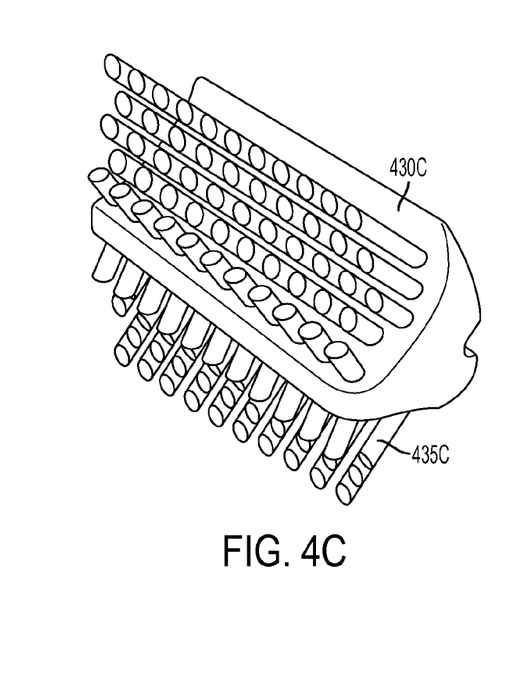

In further illustration, FIG. 4 shows front (A), top (B), and isometric (C) views of the posterior section of a bristle strip. The posterior section of a bristle strip contacts mostly the posterior teeth. In one embodiment, this section can be approximate rigid or stiff and approximately straight. Each view illustrates a bristle strip 430A, 430B, 430C having bristle bundles 435A, 435B, 435C. The front view (A) also shows a cutout 411 which can allow the posterior bristle section to move in a sliding motion along a rail on the inner and outer guard. The top view (B) further shows at least post 407. The post 407 increases the adhesion of the posterior sections to the anterior section of a bristle strip. In other words, the post 407 can connect the anterior bristle strip section to the posterior section. The post 407 can provide something for the softer plastic of the anterior section to mold around. Of note, though FIG. 4 illustrates an embodiment of a posterior bristle section, each bristle section (posterior or anterior) has a similar cross-section.

Each individual bristle strip can be composed of individual bristles arranged in groups of bristles. Note, as used, the term bristle can also refer to a bundle or a group of bristles. Each bristle bundle 435A, 435B, 435C can be attached to the bristle strip 430A, 430B, 430C by several different methods, including stapling and fusing. The bristle bundles 435A, 435B, 435C can be not detachable from the bristle strip 430A, 430B, 430C. Each bristle strip 430A, 430B, 430C can be made from plastic, including polypropylene or rubber. The individual bristles can be made of a variety of materials, including nylon, natural fibers (such as boar's hair or wood), and thin metal (such as titanium). Of note, the layout of the bristles bundle 435A, 435B, 435C as they are attached to a bristle strip 430A, 430B, 430C is not limited to a specific layout. In an embodiment, the bristles toward the front of the mouth can be higher than the bristles in the back of the mouth, since anterior teeth are longer than posterior teeth. Of further note, the bristle bundles 432, 433 on the posterior section are located on a different face then the cutout 411.

In an embodiment, the bristle bundles 435A, 435B, 435C can be positioned to have an angle of approximately 45° to the long axis of the tooth and are of different lengths. The longer bristle bundles 433 can clean the facial or lingual faces of teeth as well as the gum line. Shorter bristle bundles 432 can clean the chewing surfaces of teeth (known as occlusal surfaces on posterior teeth and incisal surfaces on anterior teeth). Of note, all bristles can be approximately perpendicular to the bristle strip, but the bristle strip itself can be angled to allow the bristles to be angled to the teeth. Of further note, a swept bristle cut may be used on the bristle bundles 435A, 435B, 435C to accommodate molar shape as illustrated in view A. Of further note, the bristles may also shorten towards the end of the bristle strip to accommodate molar width, which is shown in view B. Also, view C shows that the ends of the bristle strips can be rounded at the ends to prevent gums from being poked by a bristle strip 430A, 430B, 430C.

Of note, FIG. 4 shows an embodiment wherein each individual bristle bundle is cut in a certain manner, but it is possible in other embodiments that each individual bristle bundle and/or each individual bristle in a bundle can be cut or shaped. For example, a bristle bundle can be shaped to have conical or angled ends. The individual bundles can also include members with longer bristles in the middle or the individual bundles themselves can include members of varying lengths.

Figure 5:
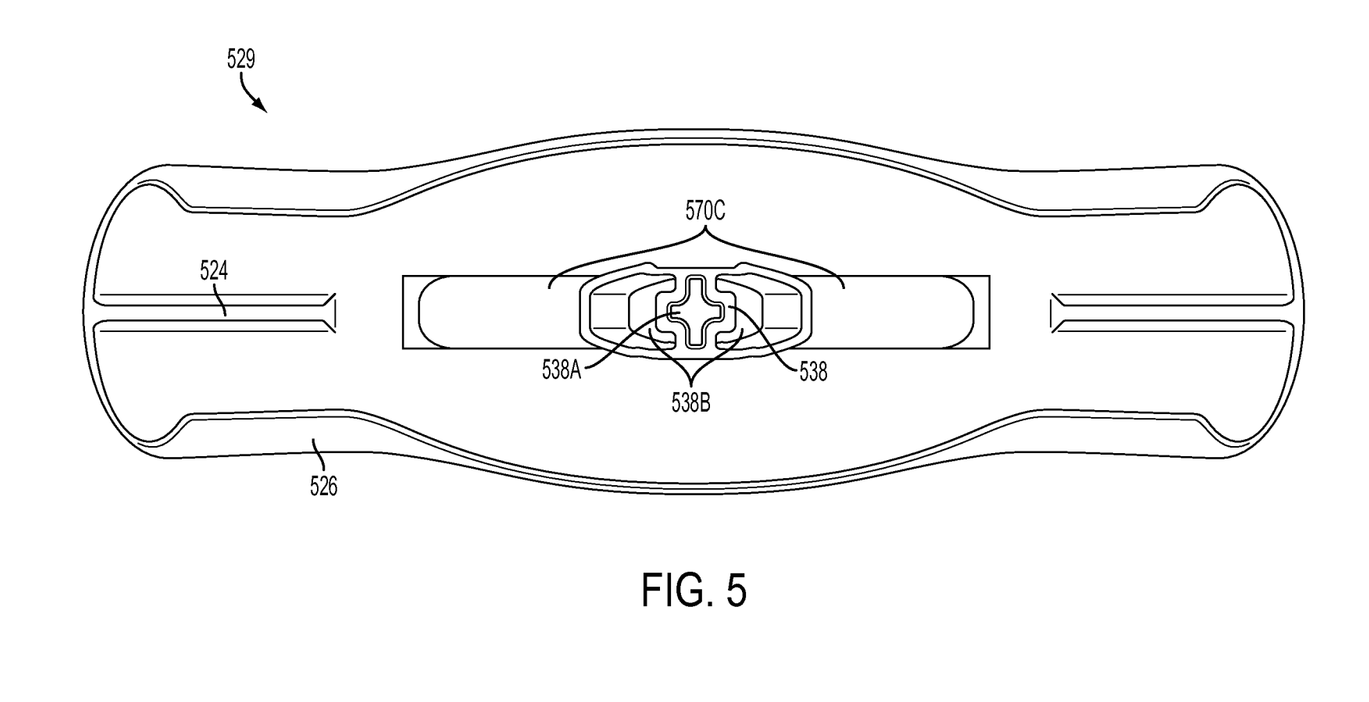
FIG. 5 is a front view of an embodiment of an outer frame component of the mouthpiece.

In further illustration, FIG. 5 is a front view of the outer frame 529 of the mouthpiece. The outer frame 529 can have a folded lip 526 to protect the gums from getting caught between the bristle strip and the frame; the folded lip 526 can also provide a bearing surface for the bristle strip to travel or move along. A bristle strip slides onto the outer frame and moves along a rail 524. In addition, coupled to the outer frame 529 is a connector/protector 538. The connector/protector 538 can have an aperture 538A that is configured to receive the connector on an inner frame. In other words, the aperture 538A can be a female press fit connector that accepts the male press fit connector of the inner frame. The connector/protector 538 also contains apertures 538B, which are configured to allow the rods of the drive assembly to move through. The apertures 570C allow the outer rods of the drive assembly to travel through.

Figure 6:
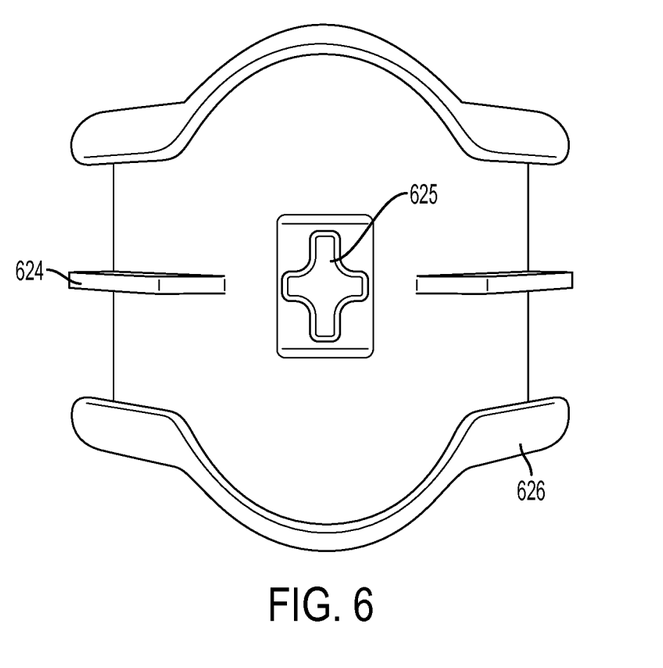
FIG. 6 shows a front view of an inner frame component of the mouthpiece in an embodiment of a full mouth toothbrush.

FIG. 6 shows a front view of an inner frame of a mouthpiece in an embodiment of a full mouth toothbrush. The inner frame can have a connector 625 that press fits into a connector/protector on the outer frame. In other words, the connector 625 can serve as an inner/outer male connector that press fits into an inner/outer female connector. A rail 624 allows a posterior section of a bristle strip to move along the frame. A folded lip 626 on the inner frame protects the gums and the tongue from getting caught between a bristle strip and the frame; it also serves as a bearing surface for the bristle strip. Of note, the inner frame has a widened front to account for the shape of an opened mouth, which allows the cleaning of hard to reach lingual surfaces of anterior teeth.

Figure 7:
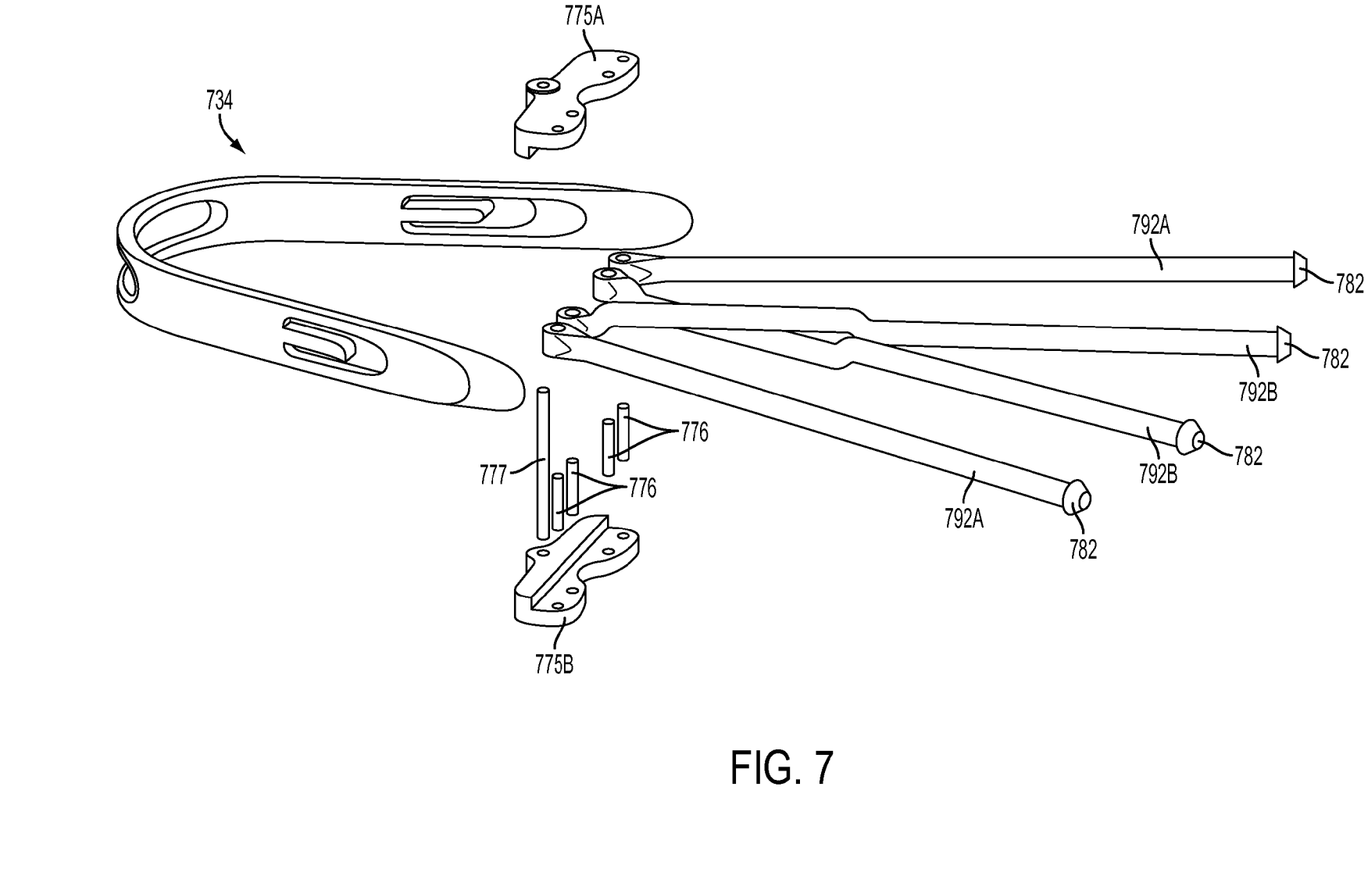
FIG. 7 is an exploded view of a portion of the drive assembly and a cover.

In further illustration, FIG. 7 is an exploded view of some of the components of a drive assembly and a cover 734 in an embodiment of a full mouth toothbrush. The cover 734 can be made of any material, including plastic that is capable of enclosing the components of the drive assembly located in the mouthpiece. Of note, in one embodiment, the cover 734 can be welded to the outer frame of the mouthpiece. In another embodiment, there can be no cover 734.

In an embodiment, the components of the drive assembly in the mouthpiece can include a plate top 775A and a plate bottom 775B that are coupled together by posts 776. Of note, the plate (the combination of the top and bottom pieces) has a customized profile to provide optimum bristle strip travel. In addition, the posts 776 fit freely through apertures configured to receive the posts 776 on outer rods 792A and inner rods 792B. The posts 776 can be press fit posts. The outer and inner rods 792A, 792B, respectively, can be rigid or flexible. In other words, the rods can be linkages, arms, cables, shafts or any other component, rigid or flexible, which can be coupled to the mouthpiece. As shown in FIG. 7, the outer and inner rods 792A, 792B, respectively, are rigid. Both the outer and inner rods 792A, 792B can have snap hooks 782 at one end (on the opposite end of where the linkage press fit posts 776 are coupled). Of further note, in one embodiment, the inner rods 792B can contain bends. The bends in the inner rods 792B can allow crossing of the inner rods 792B in the same plane, specific bristle strip motion, including a counter reciprocating motion, and a reduction in vibration. Of note, though FIG. 7 shows an example full mouth toothbrush with four rods, there is no requirement that a full mouth toothbrush have four rods.

In one embodiment, the snap hooks 782 can be coupled to the posterior portion of the bristle strip; in another embodiment, the snap hooks 782 can be coupled to a different portion of the bristle strip. In other words, the snap hooks 782, and thus the rods, can be connected to any portion of the bristle strip. Also of note, the snap hooks 782 along with each rod (outer and inner) are located in the mid-plane and are approximately symmetric, which allows for the mouthpiece to be inserted into the handle in either orientation. In another embodiment, the mouthpiece might have to be placed into the handle with a specific orientation as the positioning of the rods and the snap hooks 782 are not limited to a specific placement.

Some of the drive assembly components can further include a shaft 777 coupled to the plate top and bottom 775A and 775B, respectively, and allows the plate to move. In one embodiment, the plate can be pushed by pins in the handle in such a way that the plate oscillates backwards and forwards; in another embodiment, the plate can be a capstan pulling cables attached a mouthpiece. Thus, instead of rods attached to a plate, the mouthpiece can be moved by cables attached to a pulley or capstan. The plate can be pushed by pins propelled by a motor assembly or the plate can be human powered. In other words, the plate can be oscillated manually as a result of the pins being driven manually. In another embodiment, the rods are not connected to a plate, but instead can be connected individually to different actuators, or the rods can be directly connected to a single actuator. In other words, in some embodiments a plate can be present; in other embodiments, there is no plate.

The plate top and bottom 775A, 775B, the posts 776, the inner and outer rods 792B, 792A, and the shaft 777 can each be made from any material, including but not limited to plastic, metal, and ceramic. In an embodiment, the plate pieces 775A, 775B can be manufactured from metal, including stainless steel, but each can also be out of any hygienic metal. In another embodiment, the plate halves 775A, 775B can be made of plastic, including a hygienic plastic. Each component of the drive assembly can be manufactured by any process now known or later developed, including injection molding, casting, extrusion, and forging.

Figure 8:
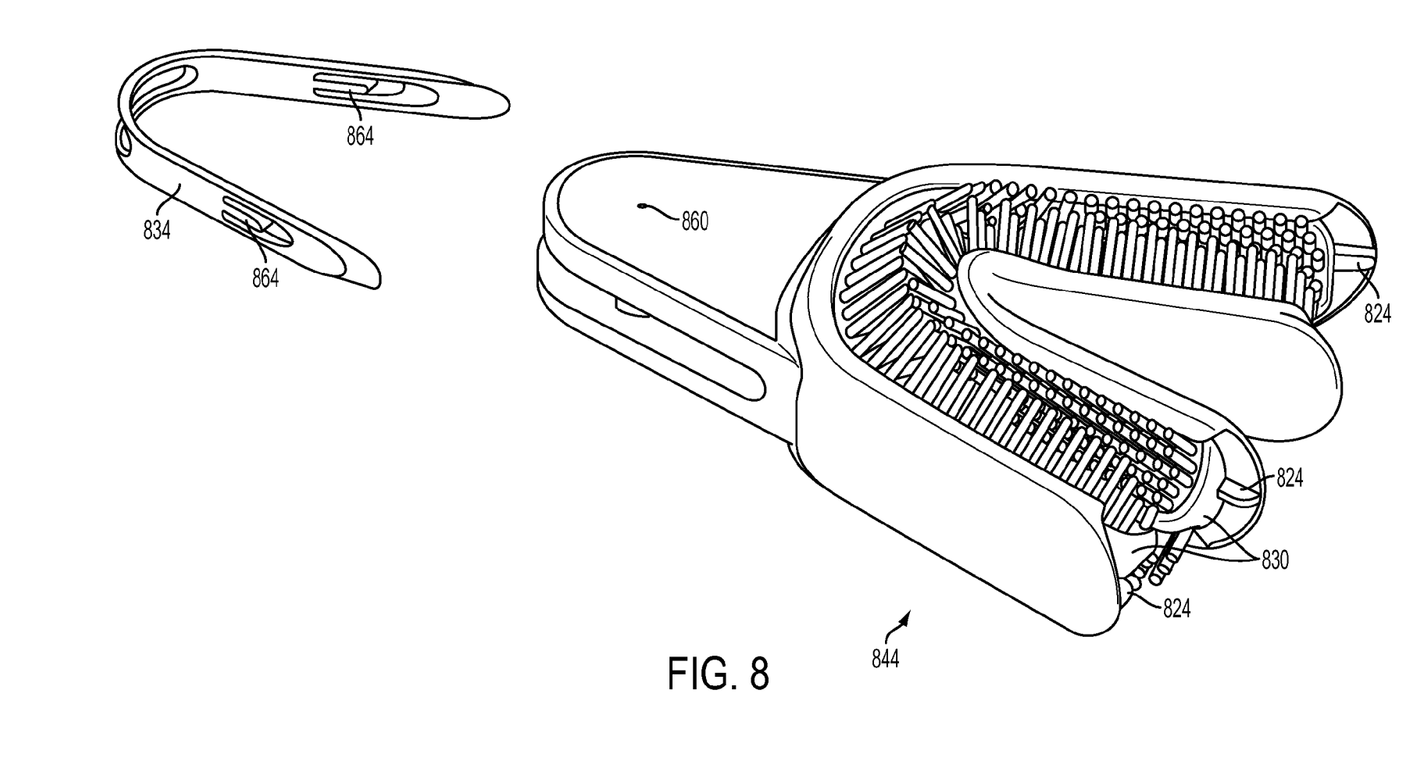
FIG. 8 shows an exploded view of the mouthpiece in one embodiment of a full mouth toothbrush.

In further illustration, FIG. 8 shows an exploded view of one embodiment of the mouthpiece 844, which can include a cover 834. The cover 834 can be welded to the mouthpiece 844. The snap hooks 864 on the cover 843 can enable the mouthpiece 844 to be secured to the handle. Of note, in another embodiment of a full mouth toothbrush, there can be no cover 834, and instead, the snap hooks 864 can be integrated into the outer frame of the mouthpiece 844 during the manufacturing of the outer frame. In addition, FIG. 8 shows bristle strips 830 on rails 824. Of note, bristle bundles in an anterior section of a bristle strip appear closer together, though in actuality they are simply just not cut away as opposed to bristles in a posterior section of a bristle strip which are shortened (for example, with a swept bristle cut or tapered bristle cut). In other words, the bristle tips in the anterior section can be longer to accommodate thinner front teeth. In addition, an aperture 860 on the outer frame of the mouthpiece 844 can be configured to receive a shaft; the shaft can be press fit into the aperture 860.

Figure 9:
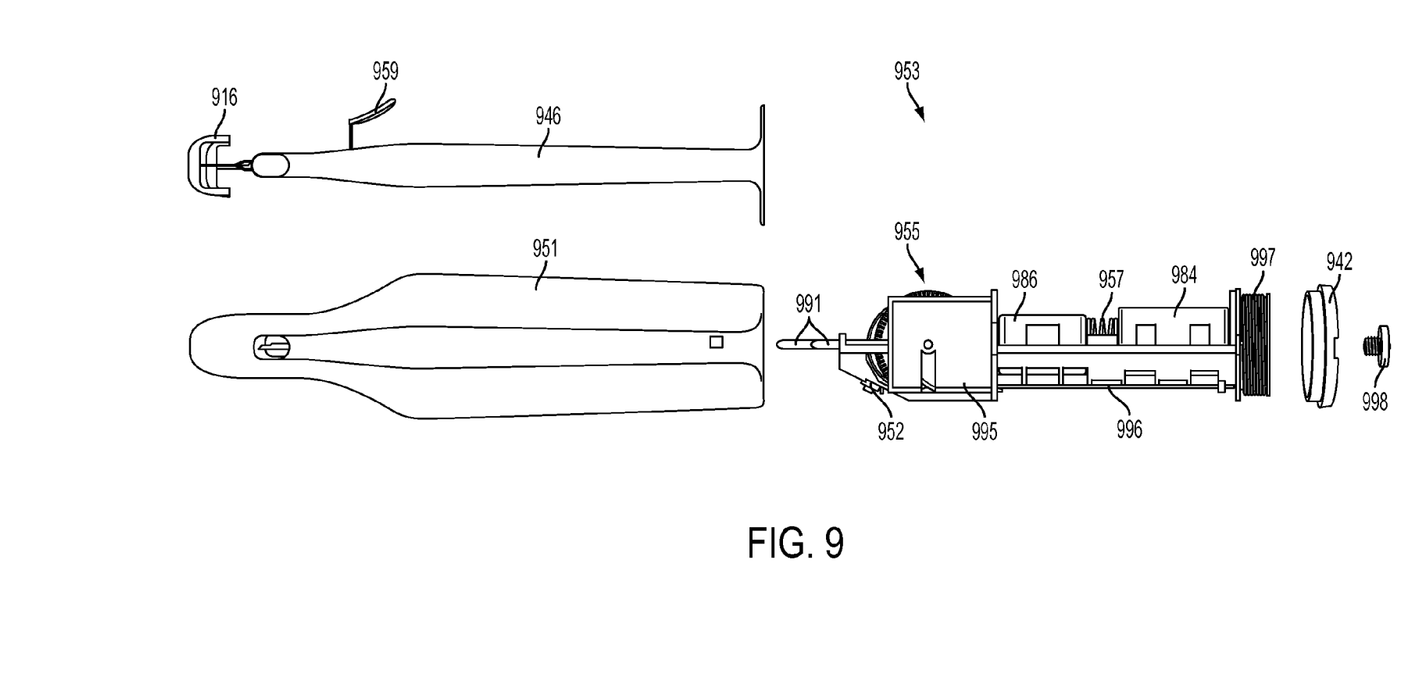
FIG. 9 is an exploded view of a handle in an embodiment of an electric full mouth toothbrush.

FIG. 9 is an exploded view of a handle in an embodiment of an electric full mouth toothbrush. As shown in FIG. 9, a gasket 916, a power button overmolding 959, and an overmolding 946 are coupled to a housing 951. Of note, all the overmolding, including the power button overmolding 959, the gasket 916, and the handle overmolding 946 can be done in a single shot; in other words, they can all be connected. The internal components 953 fit into the housing 951. A cap 942 in which a screw 998 can be threaded into a chassis 995 can assist in affixing the internal components 953 to the housing 951. Of note, additional components on the chassis 995 can also assist with coupling the chassis 995 to the housing 951. The chassis 995 can serve as a base for some of the components of the drive assembly. The chassis 995 can be manufactured from any material now known or later developed; in one embodiment, it is made of plastic.

The chassis 995 can include a charging coil 997, for example an induction charging coil. Of note, the coil 997 enables a watertight seal on the handle. Coupled to the charging coil 997 can be a power source 984, for example a battery. The battery can be is a rechargeable 4/5C nickel metal hydride (NiMH) battery. In other embodiments, the power source 984 can include a pack of multiple batteries or a single battery, which can be rechargeable or non-rechargeable and of any type, including but not limited to alkaline, nickel cadmium (NiCd), zinc chloride, silver oxide, and lithium ion.

Coupled to the power source 984 can be a spring 957, such as a compression spring, that is coupled to a motor 986. In an embodiment, the motor can be a 4000 rpm motor. A portion of the drive assembly 955, which can include pins 991, can be coupled to the motor 986. Of note, the motor 986 can be a component of a motor assembly, where the motor assembly can interface with a drive assembly 955 translating the motion of the motor assembly along one axis of rotation onto a different axis of rotation. A printed circuit board (PCB) 996 is also coupled to the chassis 995. A power button 952 is also coupled to the chassis 995.

Figure 10:
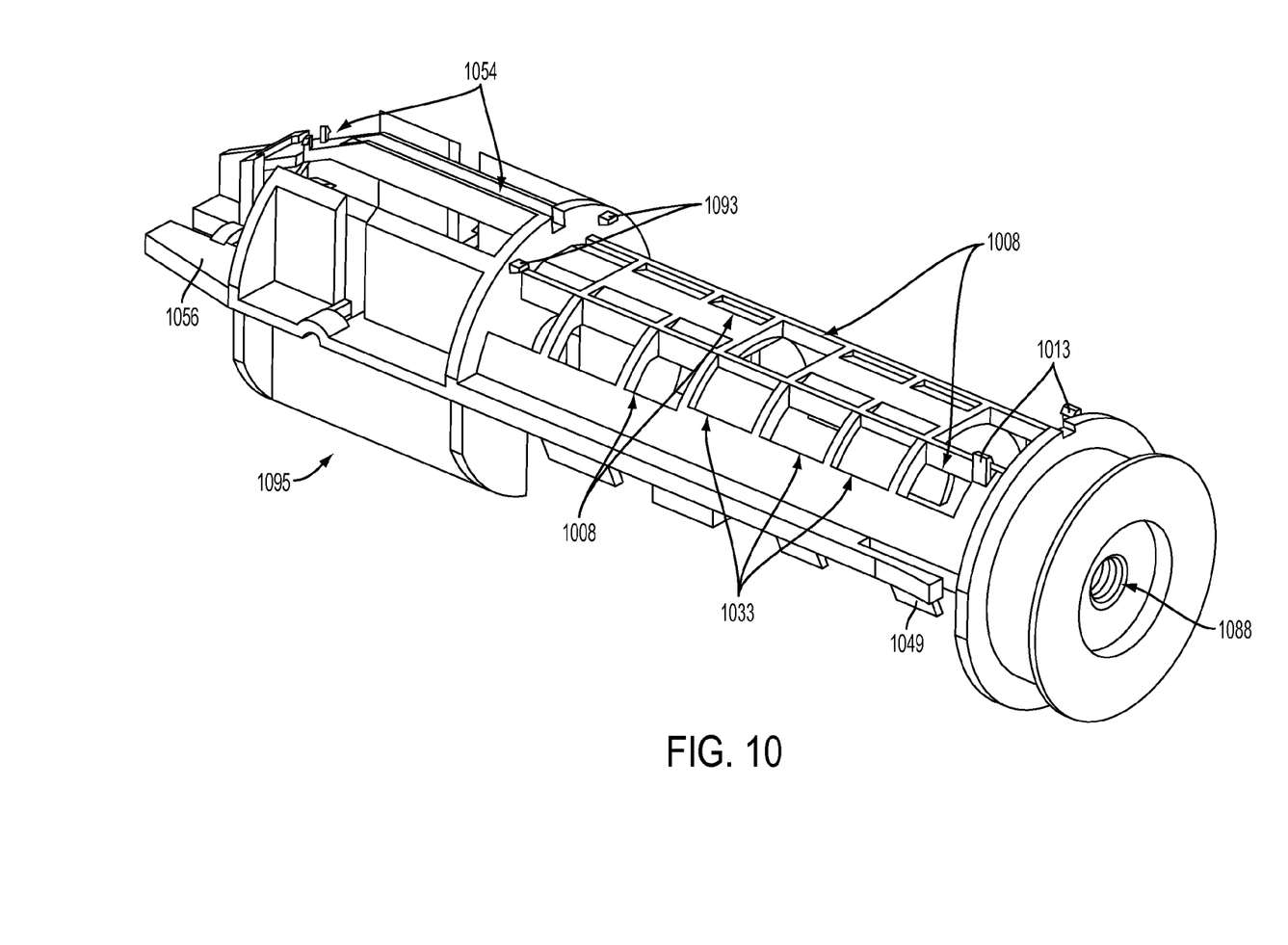
FIG. 10 shows an isometric view of a chassis configured to hold the internal components of the handle.

In further illustration, FIG. 10 shows an isometric view of the chassis 1095. The chassis 1095 can contain a threaded hole 1088 for which a screw can be configured to fit. The screw can assist in securing the chassis 1095 and the other internal components to the handle by preventing movement of the chassis 1095 further into the handle past a certain point. In addition, snap hooks 1049 can also hold the chassis 1095 within the handle, preventing it from moving out of the handle once it is inserted. Additional snap hooks 1013 as well as PCB retention/assembly features 1093 can retain a PCB. Apertures 1008 can provide openings so that battery leads can be connected to a PCB. Pin supports 1056 provide support for the pins during assembly. In addition, the chassis 1095 can provide power button support and a wiring channel 1054. Of note, the chassis 1095 can also contain recessed sections 1033 for sink prevention and for creating a more light-weight handle.

Figure 11:
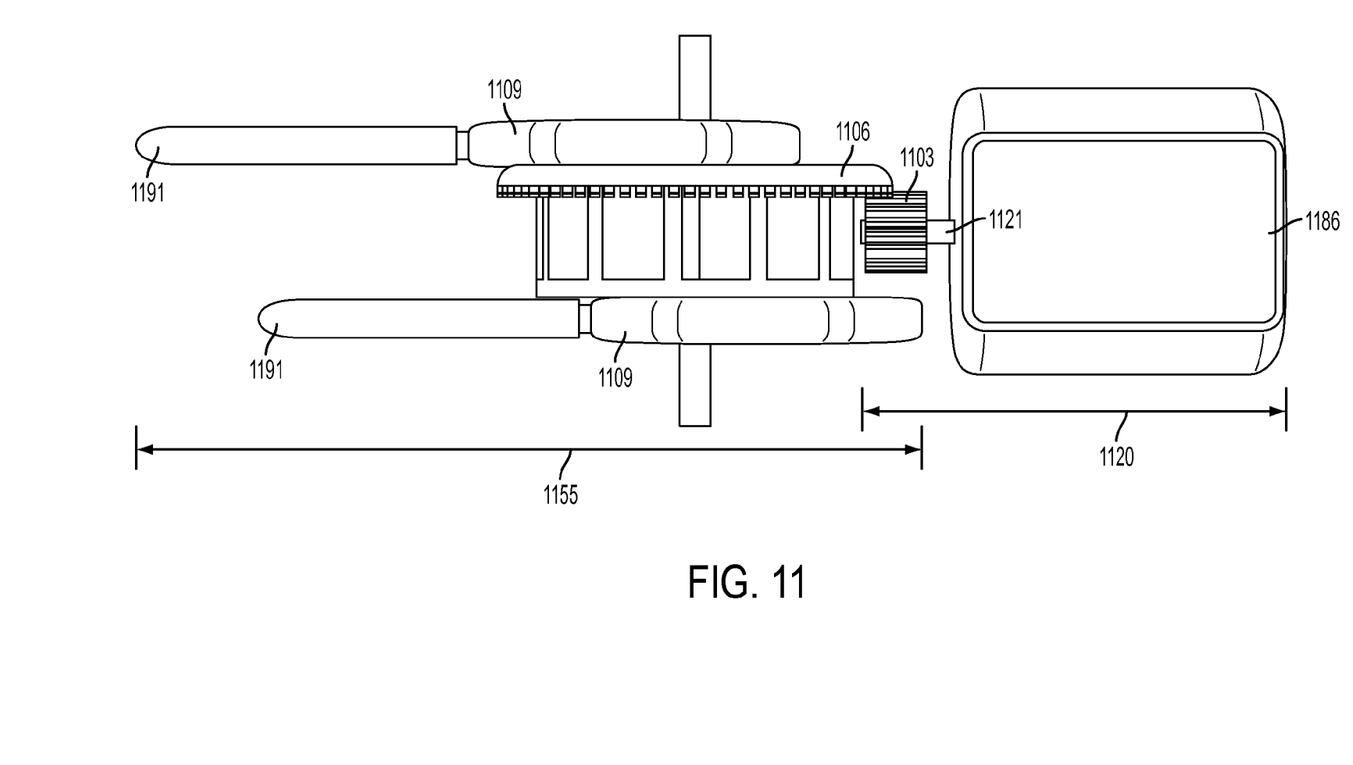
FIG. 11 shows a top view of a portion of the drive assembly and a motor assembly in an embodiment of a full mouth toothbrush.

In further illustration, FIG. 11 shows a top view of a portion of a drive assembly 1155 coupled to a motor assembly 1120 in an embodiment of a full mouth toothbrush. The motor assembly can include a motor 1186 coupled to one end of a shaft 1121. The opposite end of the shaft 1121 interfaces with a gear 1103, such as a spur gear. In an embodiment, the gear 1103 can be an eleven tooth spur gear. The gear 1103 of the motor assembly 1120 can be perpendicularly interfaced with a gear 1106 of the drive assembly 1155. In an embodiment, the gear 1106 can be a seventy-five tooth bevel gear. Coupled to the gear 1106 can be an eccentric drive ring 1109 which can be coupled to pins 1191. Of note, it is the interaction between the motor assembly 1120 and the drive assembly 1155 that transforms rotational motion into reciprocating linear motion. In operation, it is the rotation of the motor shaft 1121 by the motor 1186 that rotates gear 1103, which causes gear 1106 to move causing the pins 1191 to move linearly in a back and forth motion oscillating the plate forwards and backwards in order to cause the rods to move forwards and backwards thereby driving a portion of the mouthpiece, for instance at least one bristle strip, forwards and backwards. Of note, the full mouth toothbrush is not limited to being driven by a motor; for instance, the pins 1191 can be driven manually, which can in turn cause the plate to be oscillated manually.

Figure 12:
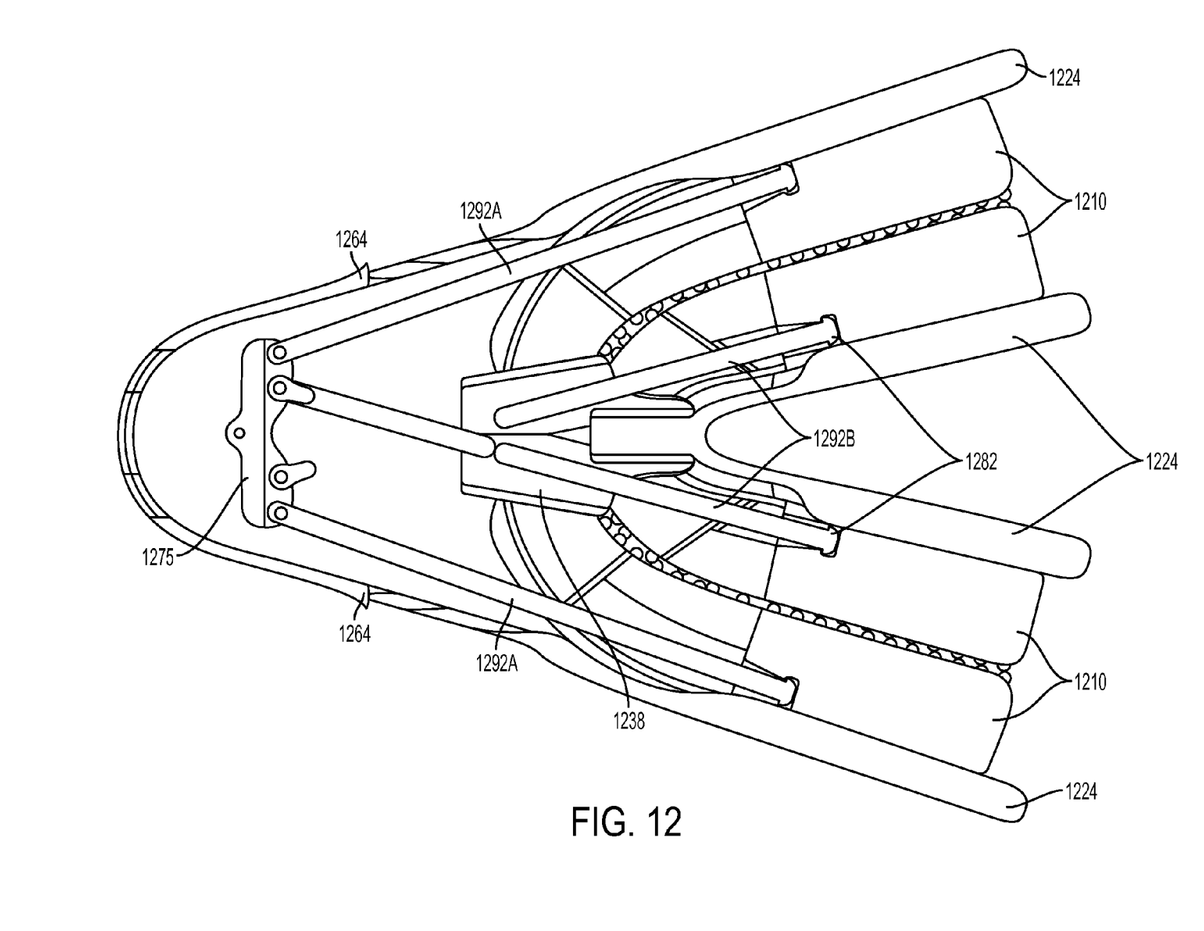
FIG. 12 illustrates a cross sectional view of a mouthpiece.

In further illustration, FIG. 12 illustrates a cross section view of a mouthpiece in an embodiment of a full mouth toothbrush. A plate 1275 is coupled to outer rods 1292A and inner rods 1292B. The inner rods 1292B pass through apertures in a connector/protector 1238. The outer rods 1292A go through at least one aperture in the mouthpiece. In an embodiment, each rod is coupled to a posterior section 1210 via snap hooks 1282 located at one end of each rod. In operation, the rods move the coupled bristle strips linearly; the bristle strips move along the rails 1224. Additional snap hooks 1264 allow the mouthpiece to be secured into a handle. When the eject buttons are pressed, the hard plastic of the handle pushes in the snap hooks 1264, thus releasing the mouthpiece from the handle.

Figure 13:
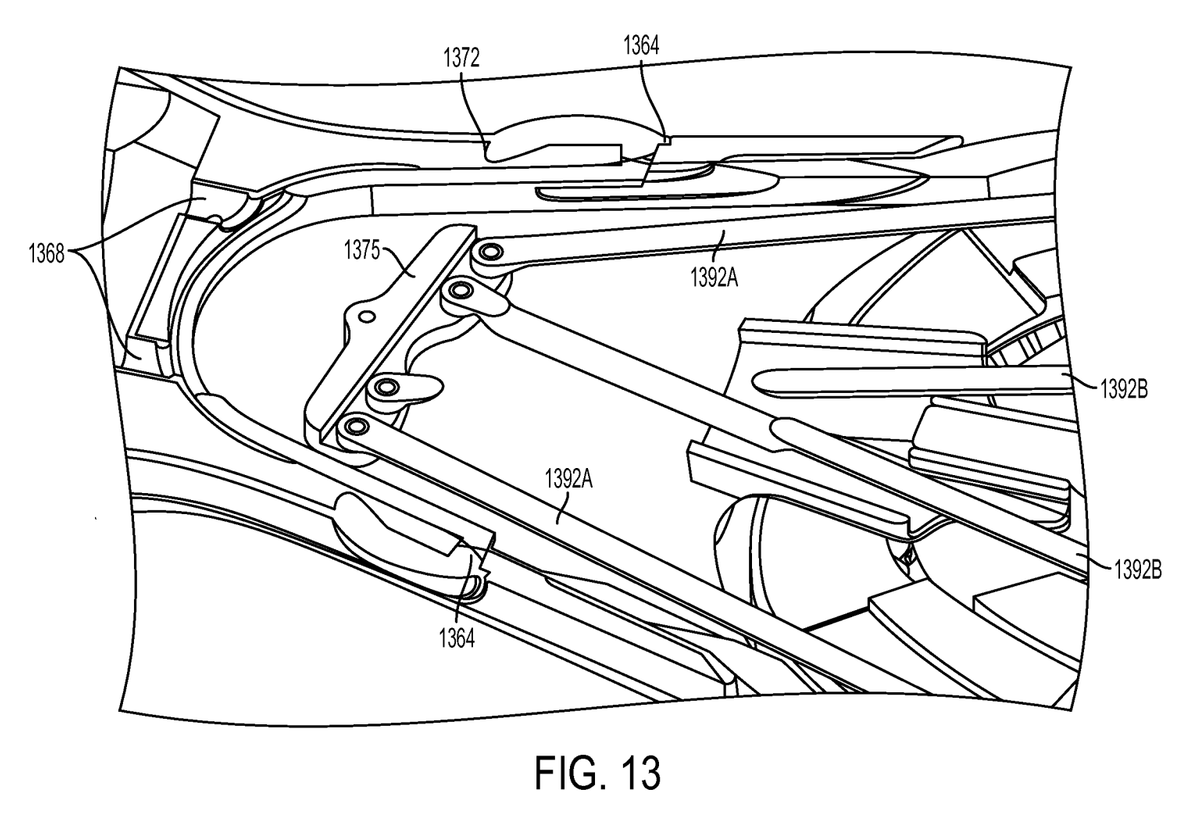
FIG. 13 shows a cross sectional view of the attachment of a mouthpiece to a handle in an embodiment of a full mouth toothbrush.

FIG. 13 shows a cross sectional view of the attachment of a mouthpiece to a handle in an embodiment of a full mouth toothbrush. The mouthpiece can contain several drive assembly components, including a plate 1375 coupled to outer and inner rods 1392A, 1392B, respectively. The mouthpiece can be secured into the handle by snap hooks 1364 that press into the soft overmolding of the handle. Living hinges 1372 on the handle allow the mouthpiece to be detached from the handle when eject buttons on the handle are pressed. In other words, the hard plastic of the handle pushes in the snap hooks 1364, thus releasing the mouthpiece. O-rings 1368 can provide an opening for the pins to enter the mouthpiece while maintaining a watertight seal inside the handle. The o-rings 1368 can also be part of the overmolding of the handle, or the o-rings can be produced separately. The o-rings 1368 can be made from plastic or from another material.

Of note, most of the parts/components referenced above can be made from any material, including plastic, metal, and ceramic. In addition, each part can be manufactured with any technique now known or later developed, including injection molding, welding, blow molding, casting, extrusion, forging, and compression molding. Of further note, the term drive assembly can refer to both components in the handle and components in the mouthpiece that are configured to move at least part of the mouthpiece, for instance at least one bristle strip.

As will be appreciated by one skilled in the art, aspects of the present invention may be embodied as a system, method, or apparatus. The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

Having thus described the invention of the present application in detail and by reference to embodiments thereof, it will be apparent that modifications and variations are possible without departing from the scope of the invention defined in the appended claims as follows.

We claimed:

1. A full mouth toothbrush comprising:
   a drive assembly for actuating a bristle strip, the drive assembly comprising pins structured to oscillate linearly;
   a mouthpiece having at least one aperture and at least one opening, the opening structured to receive the pins of the drive assembly, the mouthpiece comprising a semi-elliptical frame having a size and dimension to fit substantially inside a user's mouth and envelope substantially all of the teeth;
   an actuatable bristle strip positioned along a length of the frame, the bristle strip shaped to simultaneously engage substantially all of a user's teeth;
   at least one linkage with the drive assembly, the linkage having a first end and a second end, wherein the first end extends through the at least one aperture and is attached to the bristle strip and the second end is in communication with the pins of the drive assembly such that oscillating motion of the pins communicates reciprocating motion to the bristle strip along the length of the frame;
   a bristle bundle attached to the bristle strip for the purpose of contacting and cleaning a user's teeth.

2. The full mouth toothbrush of claim 1, further comprising a motor that actuates to the drive assembly.

3. The full mouth toothbrush of claim 2, further comprising a power source that provides power to the motor.

4. The full mouth toothbrush of claim 3, wherein the power source is a battery.

5. The full mouth toothbrush of claim 3, wherein the power source is an alternating current electrical power source.

6. The full mouth toothbrush of claim 1, wherein the bristle strip comprises a slot that slidingly engages a rail of the frame.

7. The full mouth toothbrush of claim 1, wherein the linkage is a substantially rigid linkage.

8. The full mouth toothbrush of claim 1, wherein the linkage is a cable linkage.

9. The full mouth toothbrush of claim 8, wherein the cable linkage engages a pulley of the drive assembly.

10. A full mouth toothbrush comprising:
a drive assembly for actuating a bristle strip, the drive assembly comprising pins structured to oscillate linearly;
a mouthpiece having at least one aperture and at least one opening, the opening structured to receive the pins of the drive assembly, wherein the mouthpiece comprises a semi-elliptical outer frame having a size and dimension to fit substantially inside a user's mouth and envelope substantially all of the teeth;
a rail on the outer frame; and
a movable outer bristle strip positioned on the outer frame, wherein the outer bristle strip defines a slot having a sufficient size and dimension to engage the length of the rail; the outer bristle strip structured to be movable by the drive assembly along the length of the rail in a reciprocating motion.

11. The full mouth toothbrush of claim 10, wherein the mouthpiece further comprises:
a semi-elliptical inner frame positioned to fit at least partially within the outer frame;
a second rail on the inner frame; and
a movable inner bristle strip positioned on the inner frame, wherein the inner bristle strip defines a slot having a sufficient size and dimension to engage the length of the second rail; the inner bristle strip structured to be movable by the drive assembly along the length of the second rail in a reciprocating motion.

12. The full mouth toothbrush of claim 11, further comprising an inner bristle bundle attached to the inner bristle strip.

13. The full mouth toothbrush of claim 10, further comprising an outer bristle bundle attached to the outer bristle strip.

14. The full mouth toothbrush of claim 10, further comprising:
a motor assembly powered by a power source, wherein the motor assembly engages the drive assembly.

15. The full mouth toothbrush of claim 14, wherein the drive assembly comprises:
a reciprocating member driven by the motor assembly; and
a linkage connecting the reciprocating member and the outer bristle strip to confer a reciprocating motion of the reciprocating member to the outer bristle strip.

16. The full mouth toothbrush of claim 14, further comprising:
a handle that houses the motor assembly and the power source; and
a power button positioned on the handle to activate the motor assembly.

17. The full mouth toothbrush of claim 16, wherein the handle may include one or more eject buttons which may be engaged to release the mouthpiece from the handle.

18. The full mouth toothbrush of claim 16, further comprising:
a base having a power cord that plugs into an electrical outlet, wherein the power source is a rechargeable battery capable of receiving electricity from the base.

19. The full mouth toothbrush of claim 10, wherein the drive assembly comprises:
a reciprocating member driven by the motor assembly; and
a linkage connecting the reciprocating member and the outer bristle strip to confer a reciprocating motion of the reciprocating member to the outer bristle strip.

20. A full mouth toothbrush, comprising:
a handle which maintains both a motor assembly and a power source;
a drive assembly actuated by the motor assembly, the drive assembly comprising pins structured to oscillate linearly;
a mouthpiece having a semi-elliptical outer frame having a size and dimension to fit substantially inside a user's mouth and envelope substantially all of the teeth, the outer frame having a first rail along the length of the outer frame; and
a movable outer bristle strip positioned about the outer frame and actuatable by the linear oscillating motion of the pins of the drive assembly, wherein the outer bristle strip comprises a relief having a size and dimension to fit onto and slide about the first rail of the outer frame such that the oscillating motion of the pins communicates reciprocating motion to the outer bristle strip along the first rail of the outer frame.

21. The full mouth toothbrush of claim 20, further comprising:
a semi-elliptical inner frame positioned to fit at least partially within the outer frame, wherein the inner frame comprises a second rail; and
an inner bristle strip positioned about the inner frame, wherein the inner bristle strip comprises a second relief having a size and dimension to fit onto and slide about the second rail of the inner frame.

22. The full mouth toothbrush of claim 21, wherein the drive assembly comprises:
at least one inner rod and at least one outer rod, each having a first end and a second end, wherein the first end is in communication with the pins of the drive assembly and the second end engages at least one of the inner and outer bristle strips.

23. The full mouth toothbrush of claim 20, wherein the outer bristle strip comprises a bristle bundle.

24. The full mouth toothbrush of claim 20, wherein the handle may include one or more eject buttons which may be engaged to release the mouthpiece from the handle.

25. The full mouth toothbrush of claim 20, further comprising:
a base having a power cord that plugs into an electrical outlet, wherein the power source is a rechargeable battery capable of receiving electricity from the base.

* * * * *